US00PP27142P3

(12) United States Plant Patent
Mazzardis

(10) Patent No.: US PP27,142 P3
(45) Date of Patent: Sep. 13, 2016

(54) BLUEBERRY PLANT NAMED 'EB 12-19'

(50) Latin Name: ***Vaccinium* hybrid**
Varietal Denomination: EB 12-19

(71) Applicant: Vincent David Mazzardis, Wilbinga (AU)

(72) Inventor: Vincent David Mazzardis, Wilbinga (AU)

(73) Assignees: Prunus Persica PTY LTD, Osbourne Parks (AU); Rolfe Nominees PTY LTD, Toowoomba, QLD (AU)

( * ) Notice: Subject to any disclaimer, the term of this patent is extended or adjusted under 35 U.S.C. 154(b) by 52 days.

(21) Appl. No.: 14/544,638

(22) Filed: Jan. 28, 2015

(65) Prior Publication Data

US 2016/0113166 P1 Apr. 21, 2016

(30) Foreign Application Priority Data

Oct. 15, 2014 (AU) ..... PBR 2014/247

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

2013/0340131 P1 12/2013 Mazzardis

FOREIGN PATENT DOCUMENTS

AU 2914/247 10/2014

*Primary Examiner* — Annette Para
(74) *Attorney, Agent, or Firm* — Randall Danskin PS

(57) ABSTRACT

A new and distinct variety of blueberry plant, which is denominated varietally as 'EB 12-19' is described, and which produces a large to very large fruit, which is ripe for harvesting and shipment very early in the season, under the ecological conditions prevailing in Yanchep Springs, Western Australia.

3 Drawing Sheets

Latin name: '*Vaccinium* Hybrid'.
Varietal denomination: 'EB 12-19'.

BACKGROUND OF THE NEW VARIETY

The present invention relates to a new, novel and distinct variety of blueberry plant 'Vaccinium Hybrid' and which has been denominated varietally hereinafter as 'EB 12-19'.

ORIGIN

The present variety of blueberry plant resulted from an ongoing development program which I have conducted to identify such plants. The purpose of this program is to improve the commercial quality of blueberry plants and other species. To this end, I have made controlled hybrid cross-pollinations in order to produce plant populations from which improved progeny are evaluated and thereafter selected.

The blueberry plant of the present application was originated by me and selected from a population of new plants growing at my farm and which is located near Yanchep Springs, in Yanchep, Western Australia. The new variety of plant was derived from a controlled cross-pollination of the seed parent, blueberry plant '8-19' (unpatented), and a pollen parent, blueberry plant 'EB 8-1' (U.S. Plant Pat. No. 25,859) during the 2009 growing season. The teachings as set forth in the pending U.S. Plant Patent Application are incorporated by reference herein. The seed parent is characterized principally by an upright bush-type plant, growth habit, and which further displays early-season flowering and produces medium to large, very firm fruit. The flowering bloom of the plant is considered to be good. On the other hand, the pollen parent, described above, is generally characterized by a spreading growth habit, and which further has a very early-season flowering date. Still further; the pollen parent produces very large fruit. In this regard, seed from the seed parent, identified above, produced approximately 1,000 plants following cross-pollination. Fruit from these new plants were first observed in 2011. I further studied the fruiting and growth habits of the newly discovered plant. A subsequent assessment conducted during the 2012 growing season led me to select the present variety for further evaluation. The subsequent evaluation included an asexual vegetative propagation, by cuttings, and which occurred during the 2013 and 2014 growing seasons. Subsequent evaluations of the newly derived plants has led me to conclude that the present variety is a distinct and new variety of blueberry plant. The present new variety of blueberry plant is considered to be novel in view of its semi-upright bush-type growing habit, large to very large fruit, and which have an excellent flavor and a noteworthy exterior appearance. The present new variety of blueberry plant displays an early flowering characteristic and a very early date of harvesting relative to the closest known varieties.

In comparison to the seed parent, the new variety has a noteworthy date of fruit maturity. In this regard, the seed parent is considered to have a fruit maturity date which is considered early in the season. However, the new variety of blueberry bush produces fruit which are mature for harvesting in the very early season, under the ecological conditions occurring in Yanchep, Western Australia. Still further, the seed parent produces fruit having a fruit size which is considered medium to large. In contrast, the new variety of blueberry plant produces fruit which are considered large to very large under the ecological conditions prevailing in Western Australia. In addition to the foregoing, the growth habit of the seed parent is considered to be upright. This is in contrast to the growth habit of the new variety of blueberry plant which is only considered semi-upright. Both the seed parent and the new variety produces fruit having a fruit shape which is considered to be globose.

In comparison to the pollen parent, the new variety of blueberry plant has a fruit maturity date which is very early in the season, and which is similar to that of the pollen parent. The fruit size as produced by the pollen parent is considered very large for the species. On the other hand, the new variety of blueberry plant produces fruit which are considered large to very large for the species. The growth habits of the pollen parent and new variety of blueberry plant are different. In this regard, the pollen parent has a spreading growth habit as opposed to the semi-upright growth habit, as displayed by the new variety of blueberry plant. Further, and with respect to the fruit shape, the pollen parent produces a fruit having a globose fruit shape as compared to a globose-flattened fruit shape as produced by the new variety of blueberry plant.

The present and new variety of blueberry plant is readily distinguishable from the most closely related variety, which is the 'Sharpeblue' blueberry plant (unpatented). In this regard, the closest known variety 'Sharpeblue' has a fruit maturity date, which is considered to be early to mid-season under the ecological conditions prevailing in Yanchep, Western Australia. In contrast, the new variety of blueberry plant, has a fruit maturity date which is considered to be very early in the season. Still further, the closest known variety, mentioned above, produces fruit having a fruit size which is considered to be only average for the species. In contrast, the new variety of blueberry plant produces large to very large fruit, and which are distinguishable from that of the closest known variety. In addition to the foregoing, the closest known variety has a growth habit which is considered to be bushy to spreading. This is in contrast to the new variety which has a growth habit which is considered to be semi-upright. Still further the closest known variety produces fruit having a fruit firmness which is considered only average for the species. However, the new and present variety of blueberry plant produces fruit having a fruit firmness which is considered to be very firm, and readily distinguishable from the closest known variety.

BRIEF DESCRIPTION OF THE DRAWINGS

The accompanying drawings, which are provided, are color photographs of the new blueberry plant.

Figure 1:
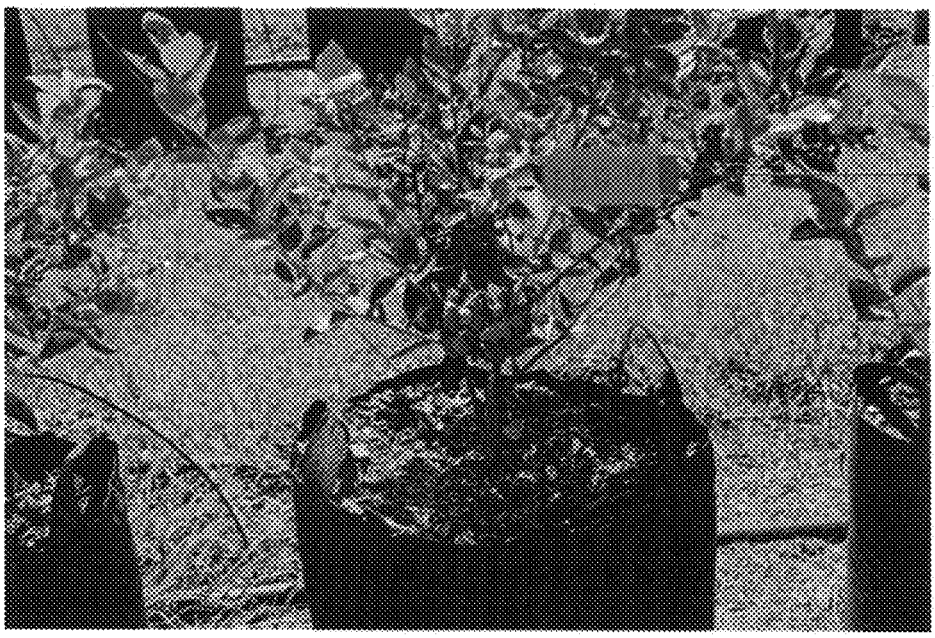
FIG. 1 illustrates the growth habit of the new variety of blueberry plant 'EB 12-19'.
Figure 2:
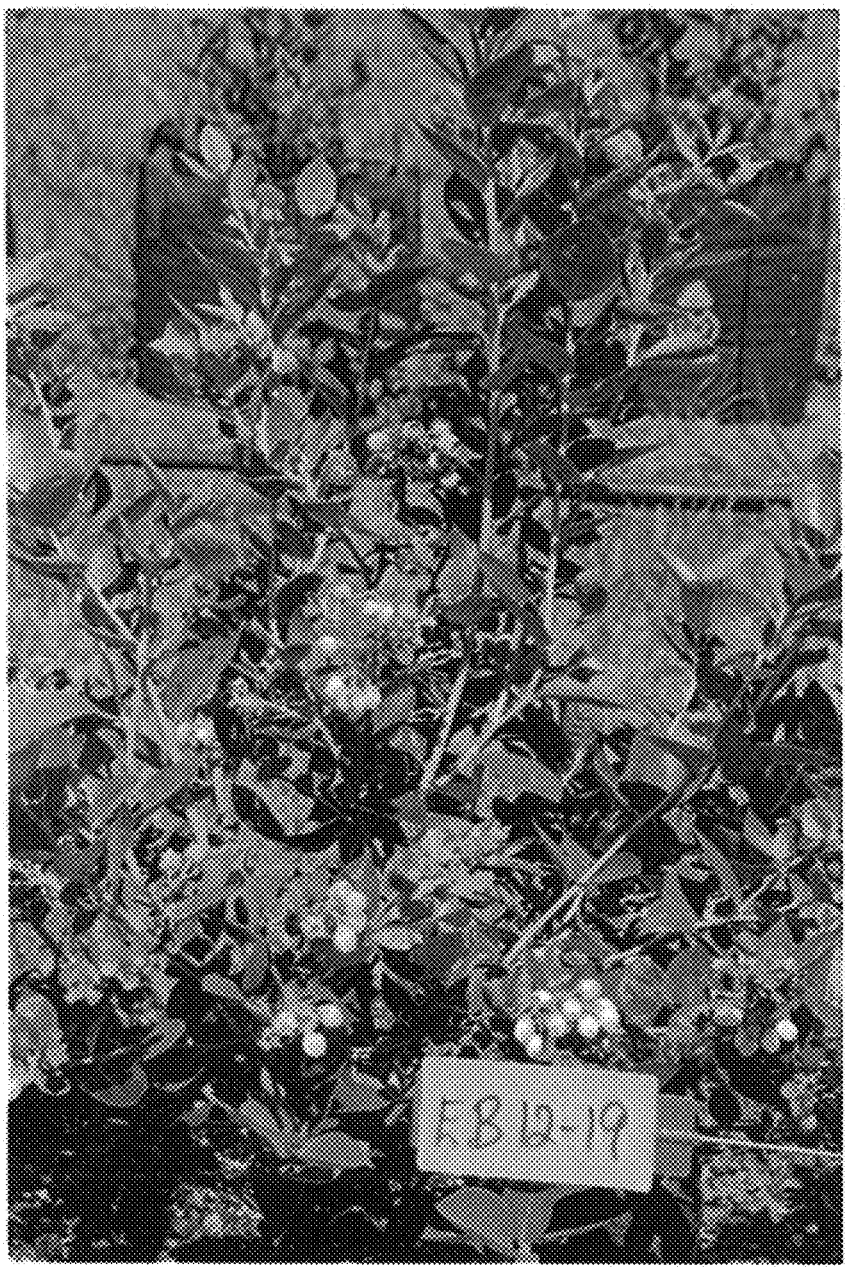
FIG. 2 shows the fruiting, and flowering characteristics of the present new variety of blueberry plant.
Figure 3:
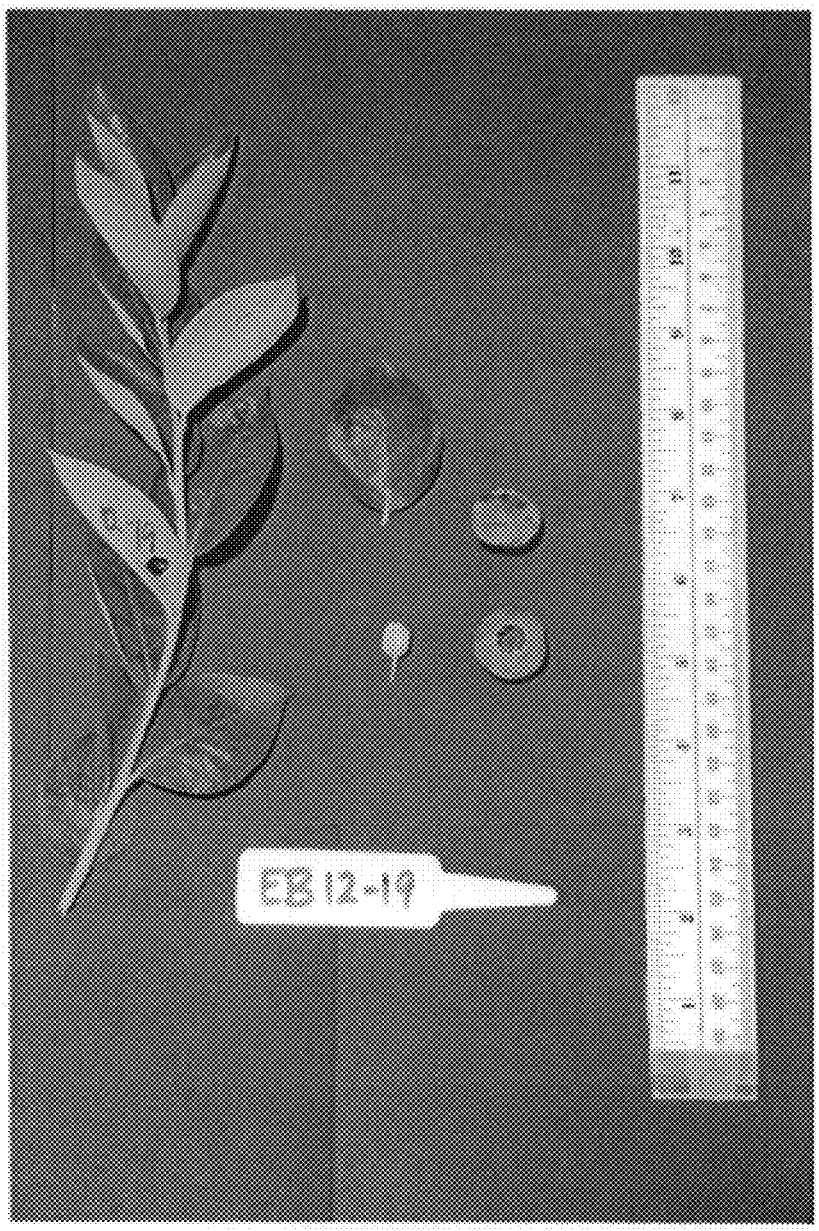
FIG. 3 shows a portion of a vegetative stem showing the growth habit of the leaves; one leaf showing the dorsal coloration thereof, and several fruit produced by the present variety.

The colors in the aforementioned photographs are as nearly true as is possible in a color representation of this type. Due to chemical development, processing and printing, the leaves and fruit depicted in these photographs may or may not be accurate when compared to the actual specimen. For this reason, any future color references should be made to the color plates and descriptions provided, hereinafter. Common color names are also occasionally employed.

NOT A COMMERCIAL WARRANTY

The following detailed descriptions were prepared to solely comply with the provisions of 35 U.S.C. §112, and does not constitute a commercial warranty (either expressed or implied) that the present variety will, in the future, display the botanical, horticultural or other characteristics as set forth hereinafter. Therefore, this disclosure may not be relied upon to support any future legal claims including, but not limited to, breach of warranty of merchantability, or fitness for any particular purpose, or non-infringement, which is directed, in whole, or in part, for the present new variety of plant.

PLANT

Referring more specifically to the botanical features of this new and distinct variety of blueberry plant, the following has been observed during the sixth fruiting season under the ecological conditions prevailing at my farm, and which is located near Yanchep Springs, Western Australia. Common color names are also occasionally used.

Plant vigor: Considered strong for the species. This is in contrast to the pollen parent as earlier identified, and wherein the plant vigor is only considered medium on average. This is still in further contrast to the closest known variety 'Sharpeblue', and wherein the plant vigor is considered medium to strong.

Plant growth habit: Considered semi-upright. This is in contrast to the pollen parent, discussed above, and which has a growth habit which is considered to be spreading. This is also in contrast to the closest known variety 'Sharpeblue', and which has an upright growth pattern.

Average size of the plant: Considered large for the species. About 1.8 meters in height and about 1.2 meters in width.

One year old shoots: Color: Green (RHS 144B).

One year old shoots: Internode Length: Considered medium to long.

LEAVES

*Leaf length.*—Considered medium to long for the species. This is in contrast to the closest known variety 'Sharpeblue', and which has medium to long leaves; and that of the pollen parent, which produces medium length leaves. The average length of the leaf is about 68 mm.

*Leaf width.*—Considered broad to very broad for the species, about 49 mm.

*Leaf shape.*—Generally speaking it is ovate.

*Leaf color.*—Dorsal Surface: Green (RHS 139A).

*Leaf color.*—Ventral Surface: Green (RHS 133C).

*Leaf color intensity.*—Considered average for the species.

*Leaf marginal edge.*—Generally considered entire.

FLOWERS

Flower bud:

*Coloration.*—Anthocyanin coloration is weak.

Open flower coloration: White (RHS NN155C).

Flower length:

*Generally.*—About 13 mm.

Flower width: About 10 mm.

Inflorescence:

*Length.*—Considered average for the species.

*Corolla.*—Shape: Urceolate.

*Corolla.*—Size: About 10 mm in length, and about 10 mm in width.

*Corolla tube.*—Coloration: Anthocyanin coloration of the corolla tube is considered absent or only very weak.

*Corolla tube.*—Surface Texture: Ridges are present on the corolla tube.

*Vegetative bud burst.*—Generally considered very early.

*Flowering on one year and older shoots.*—Considered very early for the species.

*Flowering time on current year's shoots.*—Considered very early.

*Intensity of bloom.*—Considered very strong.

FRUIT

Fruit cluster:

*Generally.*—Considered medium to dense for the species.

*Ripe fruit color.*—Yellow/green (RHS N144C).

*Unripe fruit color intensity.*—Considered average.

*Fruit size.*—About 22 mm in diameter.

*Fruit shape.*—Longitudinal sectional view — oblate.

*Sepal orientation.*—Considered erect to semi-erect.

*Sepal type.*—Considered straight.

*Calyx diameter.*—About 6 mm.

*Calyx basin depth.*—Considered deep for the species, about 2 mm.

*Fruit skin coloration.*—Black group (RHS 203D).

*Fruit flesh coloration.*—Green (RHS 138D).

*Seed coloration.*—Brown (RHS N200A).

Fruit firmness:

*Generally.*—Considered very firm

*Fruit sweetness.*—Pleasant and viewed as high, or to very high. .

*Fruit acidity.*—Low for the species.

*Fruiting type.*—Typically seen on one year old and current season shoots.

*Beginning of fruit ripening on one year old shoots.*—Considered very early for the species.

*Beginning of fruit ripening on current year's shoots.*—Considered very early.

*Harvesting date.*—In late November under the ecological conditions prevailing in Yanchep, Western Australia.

Resistance to insects and diseases: No particular susceptibilities were noted. The present variety has not been tested to exposure to detect any susceptibilities or resistance to any known plants and/or fruiting diseases.

Although the new variety of blueberry plant possesses the described characteristics when grown under the ecological conditions prevailing near Yanchep, Western Australia, it should be understood that the variations of the usual magnitude, and characteristics incident to changes in growing conditions, fertilization, pruning, pest control, frost, climatic variables, and horticultural management are to be expected.

Having thus described and illustrated my new variety of blueberry plant, what I claim as new and desire to secure my plant letters patent is:

1. A new and distinct variety of blueberry plant, substantially as illustrated and described and which is characterized principally as to novelty by producing a fruit which matures very early in the season, is considered large to very large, and wherein the plant has a semi-upright growth habit, and which is further harvested very early in the season under the ecological conditions prevailing near Yanchep Springs, Western Australia.

* * * * *